(12) United States Patent
Agarwal

(10) Patent No.: US 11,460,990 B2
(45) Date of Patent: Oct. 4, 2022

(54) PRECISE POSITIONING OF A MARKER ON A DISPLAY

(71) Applicant: KONINKLIJKE PHILIPS N.V., Eindhoven (NL)

(72) Inventor: Ankit Agarwal, Gangtok (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 75 days.

(21) Appl. No.: 17/050,006

(22) PCT Filed: Apr. 11, 2019

(86) PCT No.: PCT/EP2019/059335
§ 371 (c)(1),
(2) Date: Oct. 23, 2020

(87) PCT Pub. No.: WO2019/206670
PCT Pub. Date: Oct. 31, 2019

(65) Prior Publication Data
US 2021/0232293 A1 Jul. 29, 2021

(30) Foreign Application Priority Data
Apr. 23, 2018 (EP) .................................. 18168746

(51) Int. Cl.
*G06F 3/048* (2013.01)
*G06F 3/04845* (2022.01)
(Continued)

(52) U.S. Cl.
CPC .......... *G06F 3/04845* (2013.01); *A61B 5/743* (2013.01); *A61B 5/748* (2013.01); *G06F 3/0488* (2013.01)

(58) Field of Classification Search
CPC .......................... G06F 3/04845; G06F 3/0488
See application file for complete search history.

(56) References Cited

U.S. PATENT DOCUMENTS 9,524,040 B2* 12/2016 Kim .................... G06F 3/04845
2007/0226656 A1* 9/2007 Zwart .................. G06F 3/0481
715/856

(Continued)

OTHER PUBLICATIONS

International Search Report and Written Opinion for International Application No. PCT/EP2019/059335, filed Apr. 11, 2019, 16 pages.

*Primary Examiner* — David E Choi

(57) ABSTRACT

The invention concerns a method for precise positioning of a marker (42) on a display. The method comprising the steps of (a) displaying a marker (42) overlaid on an image on a display, wherein the marker (42) indicates a first point (43); (b) obtaining the coordinates of a second point (44) on the display (5), in response to a user input event (64); (c) determining the coordinates of a third point (54) on the display (5), said third point (54) being located at a defined distance (52) from the first point (43) in a direction (48) defined by connecting the first and second points (43, 44); and (d) moving the marker (42) from the first point (43) to the third point (54), so that the marker (42) indicates the third point. The invention also relates to a computer program, a computer-readable medium (9) and an image evaluation device (1).

14 Claims, 4 Drawing Sheets

(51) Int. Cl.
*A61B 5/00* (2006.01)
*G06F 3/0488* (2022.01)

(56) References Cited

U.S. PATENT DOCUMENTS

| | | |
|---|---|---|
| 2010/0321324 A1 | 12/2010 | Fukai et al. |
| 2013/0234964 A1* | 9/2013 | Kim .................. G06T 11/60 345/173 |
| 2013/0324850 A1 | 12/2013 | Petruzzelli et al. |
| 2016/0034129 A1* | 2/2016 | Ikeda .................. G06F 3/0416 345/168 |
| 2021/0089801 A1* | 3/2021 | Durandet ............ G06F 3/04842 |

* cited by examiner

PRECISE POSITIONING OF A MARKER ON A DISPLAY

RELATED APPLICATIONS

This application is the U.S. National Phase application under 35 U.S.C. § 371 of International Application No. PCT/EP2019/059335, filed on Apr. 11, 2019, which claims the benefit and priority of European Application No. 18168746.8, filed Apr. 23, 2018. These applications are hereby incorporated by reference herein, for all purposes.

FIELD OF THE INVENTION

The invention relates to a method for precise positioning of a marker on a display, a computer program, a computer-readable medium, and an image evaluation device configured to perform the inventive method.

BACKGROUND OF THE INVENTION

In analyzing medical images, it is customary to perform quantitative measurements on the medical images, such as measuring the length and width of anatomical structures, such as cysts, lesions or tumors. Such measurements are often performed by the radiologist positioning measurement cursors on either side of the structure whose length is to be measured, and taking the distance in between the two cursors. In this and other kinds of quantitative diagnosis, it is important that cursors are placed exactly at the position desired by the user.

In the prior art, such measurement cursors are usually positioned by use of a trackball or computer mouse. In touch-based devices, the only possible way to move a cursor is by dragging it manually using fingers. Dragging the cursor manually, however, cannot achieve the necessary precision, and both the usual width of a human finger and the limited sensitivity of the touch-based display limit the user's control over the movement of the cursor. Another disadvantage is that, when the user moves a cursor manually using his finger, he will be covering the imaging area with his own hand and will thus be unable to see where he wants to place the cursor. This also leads to inaccurate measurements. Even when using a computer mouse to place cursors on a medical image displayed on the display, it is difficult to position the marker precisely, because the mouse does not always react to movement as anticipated by the user.

Thus, there is a need for improving on the known methods of positioning cursors on a display.

US 2007/0226656 A1 discloses a graphic user interface comprising an interactive area for interacting with the user. The graphic user interface is arranged to position a cursor within the interaction area, wherein a precision interaction point is assigned to the cursor in order to enable said positioning. The precision interaction point is defined as a preset fraction of a distance between a user definable stationary interaction point and a user definable moveable interaction point. Preferably, both points are indicated to the user during the procedure of setting the precision interaction point, as well as the actual position of the precision interaction point for a visual feedback. In case the user is not satisfied with the current position of the precision interaction point, he further moves the movable interaction point, thus repositioning the precision interaction point until his satisfaction. Thus, US 2007/0226656 A1 defines a precision interaction point not by one cursor, but by two cursors, namely the stationary interaction point and the moveable interaction point. However, the problems mentioned above remain, namely that these interaction points cannot be positioned with the necessary accuracy, especially on touch-based devices.

OBJECT OF THE INVENTION

It is therefore an object of the invention to provide a method of positioning a cursor on a display with very high precision.

It is a further object of the invention to provide a method for moving a cursor on a display in a highly controlled manner. It is also an object of the invention to provide a respective computer program, computer-readable medium and an image evaluation device allowing precise positioning of a marker on its display.

SUMMARY OF THE INVENTION

To better address one or more of the above-identified concerns, in a first aspect of the invention a method for precise positioning of a marker on a display is presented in claim 1. Useful embodiments are set out in the dependent claims.

In accordance with this first aspect, the method for precise positioning of a marker on a display comprises the steps of: displaying an image and a marker overlaid on the image on a display, wherein the marker indicates a first point on the display;
obtaining the coordinates of a second point at a second position on the display, in response to a user input event indicating the second position;
determining the coordinates of a third point on the display, said third point being located at a defined distance from the first point in a direction pointing from the first point to the second point; and
moving the marker from the first point to the third point, so that the marker indicates the third point, thereby correcting the position of the marker on the display in response to the user input event.

The invention advantageously allows correcting the position of a marker on a display in response to a user input event at a second point or second position on the display. The direction defined by the position of the second point in relation to the marker position (the first point) is then used to move the marker by a defined, or optionally configurable, distance to a third point. In useful embodiments, such a defined distance will be relatively short, e.g. one or several pixels of the display, so that the marker position is moved by a small amount in the direction of the user input event. In particular, the defined distance is relatively short in comparison with the displayed image and/or in comparison with the distance between the first and second point, for example less than 20 pixels, preferably less than 10 pixels, more preferably at most 3 pixels and most preferred one pixel of the display. Thus, the invention allows to correct the position of the marker in small increments. This method provides the user, e.g. a radiologist analyzing a medical image, with a way to perform quantitative analysis of the images by precisely positioning of markers, and allows the flexibility to move the marker in any position by a defined distance.

The final coordinates of the third point are used in some embodiments to perform a measurement on the image displayed in the display. Thus, the invention is useful for precise measurements in areas of application where very accurate measurements and marker positioning is necessary, and errors cannot be tolerated. This is often the case when length measurements are performed on critical anatomical structures on medical images, such as tumors, partially obstructed blood vessels, fetuses etc. Thus, the coordinates of the third point may be used to perform length measurements on the image, in which case usually two or more markers are precisely positioned by means of the inventive method. However, the inventive method may further be used for determining a region of interest in the image, zooming in and out of areas in the image, delineating the borders of certain structures on the images, or moving annotations/labels around the display. Thus, the invention may be advantageously applied to any function requiring the accurate movement of elements such as markers on the screen.

When applying the method of the invention, the user does in most embodiments not "drag-and-drop" the marker. Instead, the user provides an input event, e.g. a touch on the display, at any second position, and the marker will move in the direction of touch relative to its own position. This makes it possible to move the marker on the display along any direction (360° in-plane) by a defined amount, in particular by a quantifiable amount. In contrast to prior art methods, the method of the invention allows to change the position of the marker incrementally, i.e. not by one "drag-and-drop" movement. Rather, the invention provides a method of correcting the marker position after it has been positioned e.g. by a prior art "drag-and-drop" method. In useful embodiments, the second position is not indicated or displayed on the display by another marker or cursor.

The display may be any device allowing the display of images and other graphical elements, such as markers. In particular, the display is a graphical display such as a screen, a monitor, a touch-screen, or a silver screen displaying optically projected images. In some embodiments, the display is part of a computer monitor, television set, tablet computer, smartphone, handheld device or the like. In useful embodiments, the display is a touch-sensitive display such as touch-screen. However, the advantages of the invention are also realized on non-touch-sensitive displays for precise measurements, as the invention allows a quantification of movement of elements or a quantification of distances which is not achievable with the usual "drag-and-drop" of cursors. For example, if the user wants to move the marker by five pixels, according to an embodiment of the invention he just needs to click on the display at any second position lying in the desired direction, and then press the mouse key five times at that position. The same result will be difficult to achieve by a trackball or touchpad usually used to move a cursor The marker may be any element, which can be displayed on the display and overlaid on an image, for example a cursor, a measurement cursor, an annotation or an arrow. In useful embodiments, the marker is a graphical element overlaid on an image and indicating a particular point or pixel on the display. The marker may e.g. take the shape of an arrow, circle, diamond, crosslines or combinations thereof, which indicate a particular point or pixel on the display. The marker indicating a point will in most embodiments be equivalent to the marker pointing to the particular point, e.g. by the center of the crosslines being positioned at that particular point of the display. Often, the marker is displayed in a contrasting color to the background image, e.g. in white, yellow or black. Alternatively, the marker may be displayed transparently, so as not to obscure the underlying image on which it is overlaid. The inventive method may also be applied to markers not designed to indicate a particular point, such as text fields, annotations, labels etc.

Obtaining the coordinates of a point on the display may in some embodiments be equivalent to obtaining the position of a point on the display, for example obtaining x- and y-coordinates of that particular point, or of the pixel of the display closest to that point. When a processor or graphics card controls the functioning of a display, it generally knows the coordinates of elements displayed on the display. Thus, also the coordinates of the first point are known in useful embodiments, and are used in determining the coordinates of the third point.

The direction connecting the first and second points can be visualized by a line connecting said points, but this line is not necessarily displayed on the display. The direction usually is the direction from the first point to the second point.

The invention thus provides a method and a related medical device to precisely position a marker, which is user-friendly, intuitive and accurate. It provides the flexibility to move the position of a marker on the display of e.g. a medical device in any direction by a defined amount.

In a useful embodiment, the length of the defined distance, by which the marker is moved along the direction connecting the first and second points, is configurable. In particular, it is configurable by information obtained through the user input event. The user input event naturally indicates the direction of movement, since the user input event indicates a certain second position on the display, and the marker is moved from the first point in the direction of the second point at the second position. Preferably, the length of the defined distance is independent of the position of the second point, and thus is not a fraction of the distance between the first and second points. The amount of movement is defined, and may be controlled or configured in various ways, for example by use of the user input event, in particular by the nature for the user input event, preferably by its duration. This embodiment advantageously allows more precise control of marker movement, wherein a user input event provides both the direction and an amount of movement. Thereby, the marker may be very quickly moved to a desired position on the display.

According to a useful embodiment, the user input event comprises at least one touch or press at the second position of the display. A "touch" is a tap on a touch-sensitive screen, e.g. with the user's finger or a stylus. A "press" is a user selection of a position on the display by means of a cursor, which is moved by a cursor-positioning device such as a mouse, a trackball or a touchpad, to a current position, and that position may be selected by a mouse click, press on the touchpad/trackball or corresponding button. All of these devices allowing a user to select a particular point or position on a screen or display, including a touch-sensitive display, are named "pointing device" in this application. According to this embodiment, the user input event indicating the second position entails the user selecting a position on the display with such pointing device (which may also be the user's finger in connection with a touch-sensitive display). The user may select said position by a tap or touch on the touch-sensitive display, or by a click or press on the cursor-movement device, such as the mouse, a trackball or touchpad, when the cursor is at the selected position. This embodiment is cost-effective in its implementation, since appropriate pointing devices are usually already present in image evaluation devices used for performing quantitative analysis of images. When the user input event comprises a touch on a touch-sensitive display or screen, advantageously the user will not have to cover the area of the marker with his/her own hand during the positioning of the marker, since the second position may be far away from the first position. Thus, advantageously the user can accurately position the marker and thereby select e.g. a control point necessary in quantitative diagnoses, without covering the measurement area with his/her hand.

In a useful embodiment of the inventive method, the defined distance has a predetermined unit length, or a multiple of said predetermined unit length. Such unit length may for example correspond to the length of one pixel of the display, but may also have another predetermined length, which usually will be a relatively short length in comparison with the displayed image. For example, the unit length may be 1-20 pixels, preferably 2-10 pixels, more preferably at most 3 pixels and most preferred one pixel of the display. By using a unit length, the user has better control of the movement of the marker, since such movement occurs by a length known to the user. As described below, the user may provide a user input event moving the marker by several unit lengths, either in one step corresponding to a multiple of unit lengths, or, more preferred, in a stepwise manner, wherein each step corresponds to a movement of the marker in the direction towards the second point by one unit length. In such embodiments, the user has complete and intuitive control over the movement of the marker.

According to a further useful embodiment, the length of the defined distance, by which the marker is being moved, is configurable by the user input event as described in the following. In an advantageous embodiment, the duration of the touch or press determines the length of the defined distance. In particular, the length of the defined distance may be longer, the longer the duration of the user input event, e.g. the length of the defined distance may be proportional to the user input event. Thus, the user can influence by the user input event whether he wants the marker to move by a small distance or by a longer distance. In a particularly useful embodiment, the marker moves such distance not in "one leap", but in a stepwise manner. For example, a "long press" or "long touch" selection triggers the movement of the marker along said direction for a plurality of steps, each having a pre-determined unit length. This is an intuitive way of correcting the marker position: If the user finds that the marker needs to be moved in a particular direction, he performs a touch or press (e.g. mouse click) at a second position which points to the correct direction, and leaves his finger on the touch-sensitive screen, or on the button of the mouse or other pointing device, until the marker has moved the desired distance. In other embodiments, the defined distance is travelled by the marker "in one leap" and the length of the defined distance is proportional to the duration of the touch or press.

According to a preferred embodiment, the marker is moved in the direction connecting the first and second points in a stepwise manner, each step preferably corresponding to a predetermined unit length. The time gap between each step is also predetermined in useful embodiments. The total length travelled by the marker in this stepwise manner may be determined by the duration of touch or press, as described above. In useful embodiments, the marker moves in a stepwise manner for the duration of the touch or press. Thus, the user touches or presses the display at the second position, holds the touch or press while the marker moves from the first point in the direction of the second point in a stepwise manner. When the marker has reached a position which the user considers appropriate, he releases the touch or press, and the movement of the marker over the display stops.

According to another optional feature of the invention, the marker is also moved in a stepwise manner, whereas each step is triggered by a single touch or press of the user input event. Thus, the user may move his finger or another pointing device to a desired second position, thereby indicating the direction in which the marker is to move. By then touching or pressing repeatedly at this position the marker will move in this direction in a stepwise manner, each step having a predetermined unit length. In a different way of describing this embodiment, the steps (a) to (d) are repeated with individual touches or presses, each being a new user input event.

In a useful embodiment, the method steps used for moving the marker from its initial position (the first point) to the corrected position (the third point) may be iterated or repeated, until the user is satisfied with the marker position. This allows precise and controlled movement of the marker on the display. Particularly in embodiments where the marker is moved by one unit length per touch or press performed by the user, the user may touch or press several times to move the cursor in a stepwise manner towards the desired final position. This embodiment is highly user-intuitive.

Accordingly, when steps (a) to (d) are iterated, the third point indicated by the marker becomes the first point. A second user input event indicates another second position. In some embodiments, the second position of the iteration may be at about the same position as in the first iteration, e.g. if the user presses or touches at the same position on the display several times, to move the marker stepwise in that direction. However, the second position in the second iteration may also be at a completely different position on the display than in the first iteration, namely if the user wants to change the direction of marker movement.

If the marker need to be moved a long way on the display, the user may in some embodiments use the already existing technology of "drag-and-drop" to move the marker near the desired position, and the use an embodiment of the invention for placing it accurately on the desired position.

According to an alternative embodiment of the invention, the length of the defined distance is configurable by the distance of the second point from the first point. For example, the longer such distance, the longer the defined distance by which the marker is moved on each iteration of method steps (a) to (d), or on each touch/press of a user input event. In this alternative embodiment, if the marker needs to travel a long way, the user touches or presses the display far away from first position, making the marker move by a long step.

In some embodiments, the length of the defined distance, e.g. the pre-determined unit length, is configurable by a further user input. For example, the length of the defined distance may be set by the user before selecting a marker to be precisely positioned. In an embodiment, such a defined distance may be stored in a specific input field, e.g. in a settings page of the image evaluation app, which is a software application incorporation a computer program executing the method. Such field may be pre-configured, and may (or may not) be configurable by the user. Accordingly, in some embodiments, the user can configure the computer program executing the method, such that the length of the defined distance, e.g. the pre-determined unit length, may be adjusted to his particular needs. Thereby, the method may be adapted to the specific requirements of various image evaluation techniques, and thereby image analysis can be accelerated.

In a useful embodiment, it is the predetermined unit length which is configurable by the further user input, e.g. the user input field in a setting page. Thus, the marker may still be moved by the multiple of unit lengths, e.g. in a stepwise manner, but the length of each step may be adjusted by the user.

In a useful embodiment, the marker is overlaid on an image displayed in an image region of the display, and the user input event indicates a second position which may be inside or outside the image region, and in particular the second position does not have to be inside the Region of Interest, i.e. that part of the image region which displays the part of the image which is of interest to the user. Thus, the user advantageously does not have to touch or press close to the initial marker position (first point), which presumably will be inside his Region of Interest. In case of a touch-based device, he would thereby obscure the image region with his own hand and would thus be unable to see where he wants to move the marker. According to this useful embodiment, he may touch the screen at any position on the display, also outside the image region, and in particular outside his Region of Interest, and thus may avoid obstructing his view of the marker and its desired final position. In some embodiments, the user will touch the display always outside the image region, which allows a constant good view and at the same time allows an exact determination of the movement direction.

According to a useful embodiment, the image displayed on the display is a medical image, wherein the invention is not limited to the modality by which the image is acquired. The medical image may be acquired by any medical imaging modality such as ultrasound (M-mode, Doppler ultrasound, three-dimensional ultrasound), magnetic resonance tomography, computed tomography, X-ray imaging, SPECT (single positron emission computed tomography), PET (positron emission tomography) or Infrared Imaging. In useful embodiment, the image comprises a two-dimensional, three-dimensional or four-dimensional dataset, such as a matrix, of pixels or voxels. The image displayed on the display may also be a diagram or graph of medical data other than images, in particular medical data acquired from a subject or patient, such as an ECG (electrocardiogram), MEG (magnetoencephalogram) or a chemical spectrum, such as an MR spectrum. Also in such graphs, it is often necessary to take precise measurements, which may be facilitated by precise positioning of markers, as achieved by the invention. The invention may be used in all fields of imaging, and may be used to furnish measurement results useful e.g. in diagnosis.

The image displayed on the display can be a two-dimensional image, or a sectional image plane through a three-dimensional image, or a rendering of a three-dimensional image. Preferably, each iteration of steps (a) to (d) for moving the marker is performed in one image plane. However, if the image plane is e.g. a sectional image plane through a three-dimensional image, the orientation of said image plane may be changed between the iterations of steps (a) to (d). Thereby, the inventive method of positioning and moving the marker may be advantageously used in the analysis of three-dimensional images.

In order to perform such measurements, in useful embodiments the coordinate of the third point will be calculated back to image coordinates, in order to determine the final position of the marker not on the display, but with reference to the image displayed.

In useful embodiments, the marker is selected by the user in some way before starting method steps (a) to (d), especially in cases where several markers are displayed on the display. Thus, the user first selects one marker for precise positioning, and the next user input event, such as a touch or mouse press, will be used to move the selected marker from its initial position (first point) to its final position (third point). In useful embodiments, the user may select each marker on the display successively for precise positioning by the inventive method.

The invention is also related to a computer program or computer program product comprising program code instructions which, when executed by a processor connected to a display, enables the processor to carry out the above-defined method, in particular the inventive method in one of its embodiments. Such a computer program may be written in any code, as it requires mostly manipulation of elements displayed on a display. The processor executing the method may be any kind of calculation device including a graphics card, a CPU, chip or other processing device. The processor may be part of a computer such as general-purpose computer, PC, workstation, control console of a medical image device, in particular an ultrasound scanner, a server, or a cloud computer. Further, the processor may be part of a hand-held device such as a tablet computer or smartphone. The processor will in useful embodiments be part of an image analysis device, which may be part of an imaging modality such as an ultrasound, MR or CT scanner. Alternatively, the method may be executed on a standalone device configured for image analysis, which is not used to control the scanner.

The invention is further directed to a computer-readable medium comprising an above-defined computer program. The computer-readable medium may be any digital data storage device, such as a USB-stick, CD-ROM, SD-card, SSD-card, hard disc. Naturally, the computer program need not to be stored on such a computer-readable medium to be supplied to customers, but may be downloaded from a distant server or cloud, e.g. over the internet.

The invention is also directed to an image evaluation device configured to perform an embodiment of the inventive method. Such image evaluation device comprises a display configured to display an image and the marker overlaid on the image, wherein the marker indicates a first point on the display. Further, the device comprises a processor as described above—configured for obtaining the coordinates of the first point and a second point in response to a user input event, and configured for determining the coordinates of a third point on the display, said third point being located at a defined distance from the first point in the direction defined by the first and second points, i.e. the direction pointing from the first to the second point. Further, the image evaluation device includes a pointing device for allowing a user to indicate the second position on the display. Any device allowing a user to select a particular point or position on a screen or display, including a touch-sensitive display, is named "pointing device" in this application. According, the pointing device may also be the user's finger in connection with a touch-sensitive display, or any other cursor-movement device, such as the mouse, a trackball or touchpad. The image evaluation device may further include additional user input devices, such as a keyboard.

Any features or useful embodiments described in connection with the inventive method also apply to the image evaluation device.

In an embodiment, the image evaluation device includes a touch-sensitive display, and thus the pointing device is constituted by the touch-sensitive display. This embodiment is particularly advantageous, since it provides an image evaluation device which may be handled highly intuitively by the user, and nevertheless provides the means for performing highly accurate measurements and movements on its display.

BRIEF DESCRIPTION OF THE DRAWINGS

The invention shall now be illustrated by means of particular embodiments with reference to the attached drawings, in which.

DESCRIPTION OF EMBODIMENTS

Throughout the figures, the same or corresponding features/elements of the various embodiments are designated with the same reference numbers.

Figure 1:
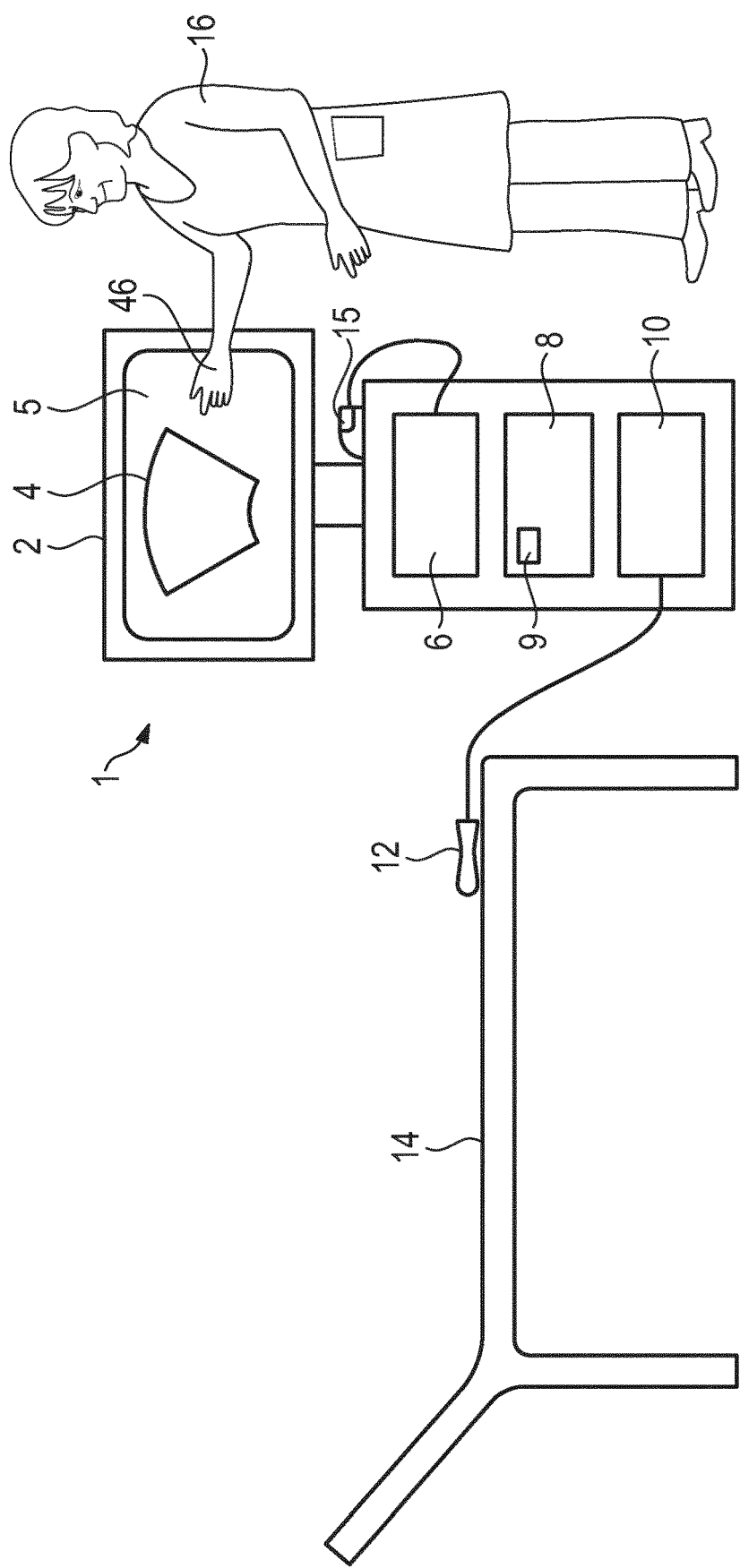
FIG. 1 shows an image evaluation device according to an embodiment of the invention.

FIG. 1 schematically illustrates an image evaluation device 1, which in this case is part of an ultrasound imaging machine or ultrasound scanner. The image evaluation device 1 includes a computer screen 2 having a touch-based display 5. An ultrasound image 4 is currently displayed on the display 5. In case the display is a touch-sensitive display, the user 16 may use his hand 46 to indicate positions on the display 5 by touch or tap with his/her finger. Alternatively, a computer mouse 15 or any other cursor-movement device (trackball, touchpad etc.) may be provided for selecting or indicating such a position on display 5.

The image evaluation device 1 further includes a processor 6, such as a CPU and/or a graphics card, which is able to control any images or elements displayed on the display 5. The processor 6 is configured to execute an embodiment of the inventive method. The image evaluation device 1 further includes a data storage medium 8, such as a hard disc, on which a computer program necessary for executing the invention on the image evaluation device 1 or its processor may be stored. Further, there may be an insertable computer-readable medium 9, e.g. USB-stick, which may be used to load the necessary computer program onto the image evaluation device 1. Finally, the image evaluation device may include an ultrasound control unit 10, which controls the acquisition of ultrasound images by the ultrasound probe 12. A patient bed 14 is provided for a subject, e.g. a patient, reclining while ultrasound images 4 are being acquired by the user 16. The user 16 may be any person who wishes to perform an accurate image evaluation, which in the case of medical images will often be a radiologist or radiographer, but can also be a specialist in any other field, such as gynecologist, a cardiologist etc. The invention provides an intuitive method which may be used by any user 16 without requiring a special training.

Figure 2:
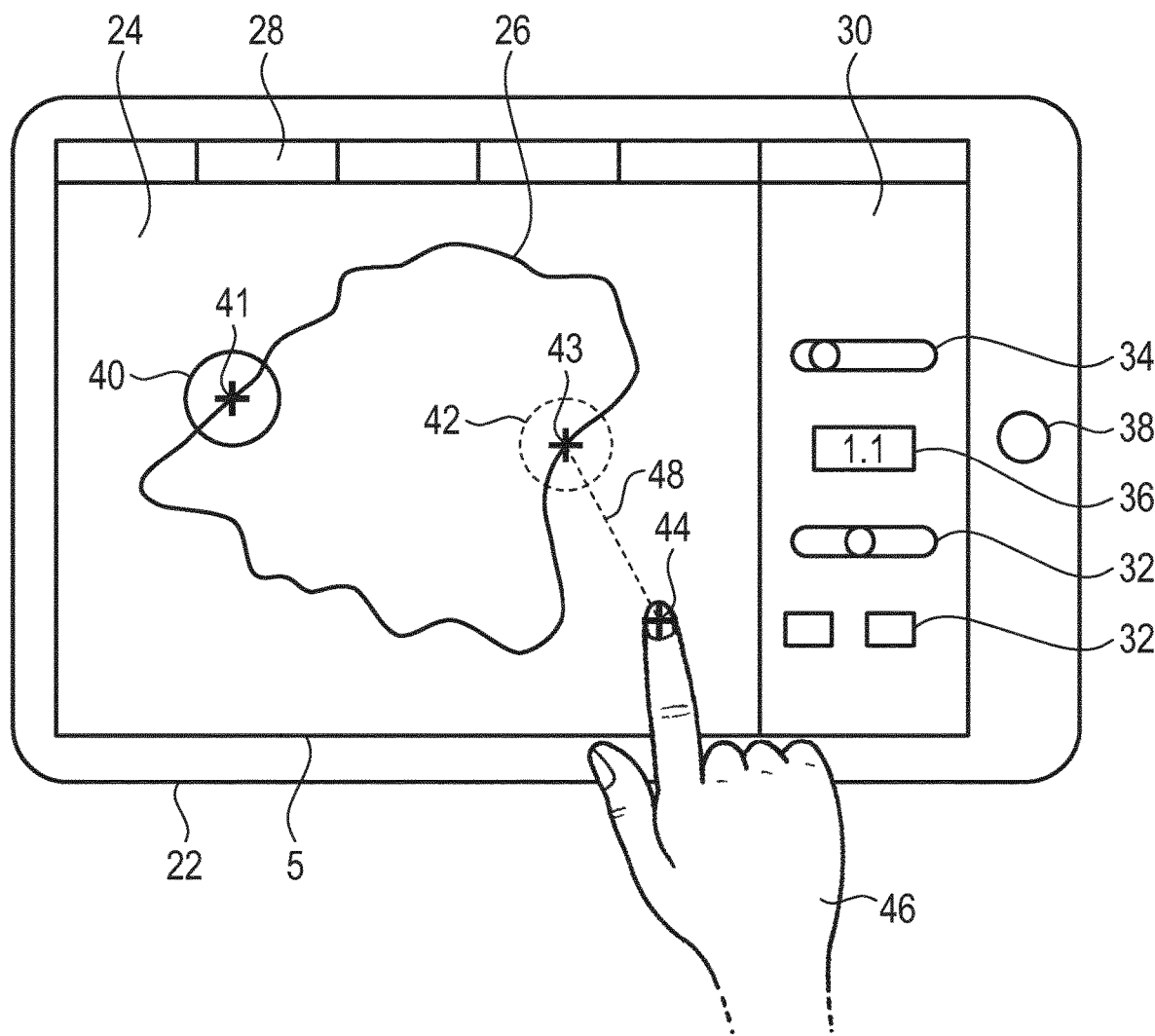
FIG. 2 shows a tablet computer having a touch-sensitive display on which an embodiment of the invention is being performed.

FIG. 2 provides a front view of a tablet computer 22, e.g. an iPad, having a touch-sensitive display 5 and a home button 38. The display 5 illustrates an embodiment of the inventive method for precise positioning of a marker: An anatomical structure 26 as part of a medical image 4 is currently displayed in an image region 24 of the display 5. A control bar 28 on the top of the display or screen is provided to accommodate further user input, for example by means of drop-down menus allowing the user to select a specific image to be analyzed, as well as further selections. To the right of the image region 24, a measurement control area 30 is situated and provides several control buttons and control sliders 32 providing various functionalities with may be used by the user to perform image analysis inside the image region 24.

In this embodiment, a user 16 may wish to position two control points 41, 43 in order to measure the width of the anatomical structure 26. Therefore, two markers or measurement cursors 40, 42 are placed inside the image region 24. Each marker consists of a circle, and at the center of the circle a star or crosslines indicating a point. The marker 40 indicates the point 41 on the left side of the anatomical structure, whereas the marker 42 indicates point 43. The initial position of each marker 40, 42 may be made a user input event, such as a touch/press event or a "drag-and-drop" event, or alternatively markers 40, 42 are initially positioned by the image evaluation device 1 at a standard position. In an embodiment, the method provides the possibility for the user to select marker 42. The selected marker 42 is shown on the display 5 e.g. in a different color, or in the example shown in a dashed line. In an embodiment, the user may first drag the selected marker 42 to a position roughly corresponding to the desired position. At this position, the marker 42 indicates position 43.

If the user 16 now wishes to correct the position of marker 42, he made tap or touch the display 5 at any position 44 with a finger of his/her hand 46. Thus, the processor may now obtain the coordinates of the first point 43, which is the initial position of the marker, and the coordinates of the second point 44. By the first and second points 43, 44, a direction is defined from the first point 43 to the second point 44, and which is indicated by the dotted line 48 in FIG. 2. Please note that this dotted line 48 is in most embodiments not displayed on the display, but shown in FIG. 2 merely for illustrating the invention. User 16 only notices that the marker 42 moves in the direction 48 by a defined distance, in particular by a predetermined unit length, with each touch or tap of his finger. If the user 16 moves his finger to a different second position 44' and taps the touch-sensitive display again, the marker 42 will move by one unit length in the direction defined by the new second position 44' (see FIG. 3).

According to an embodiment of the invention illustrated in FIG. 2, the user has the means to adjust the unit length by which the marker 42 moves with every tap or touch. In this embodiment, the unit length in pixels is stored in the input field 36 within the measurement control area 30. In the example shown, the unit length is 1.1, which may indicate 1.1 pixels. The content of the input field 36 may be changed either by inserting a different number by means of a keyboard, or by manipulating the slider 34, for example, actuating the slider 34 may change the value for the unit length in field 36 between 0.5 and 10.

Figure 3:
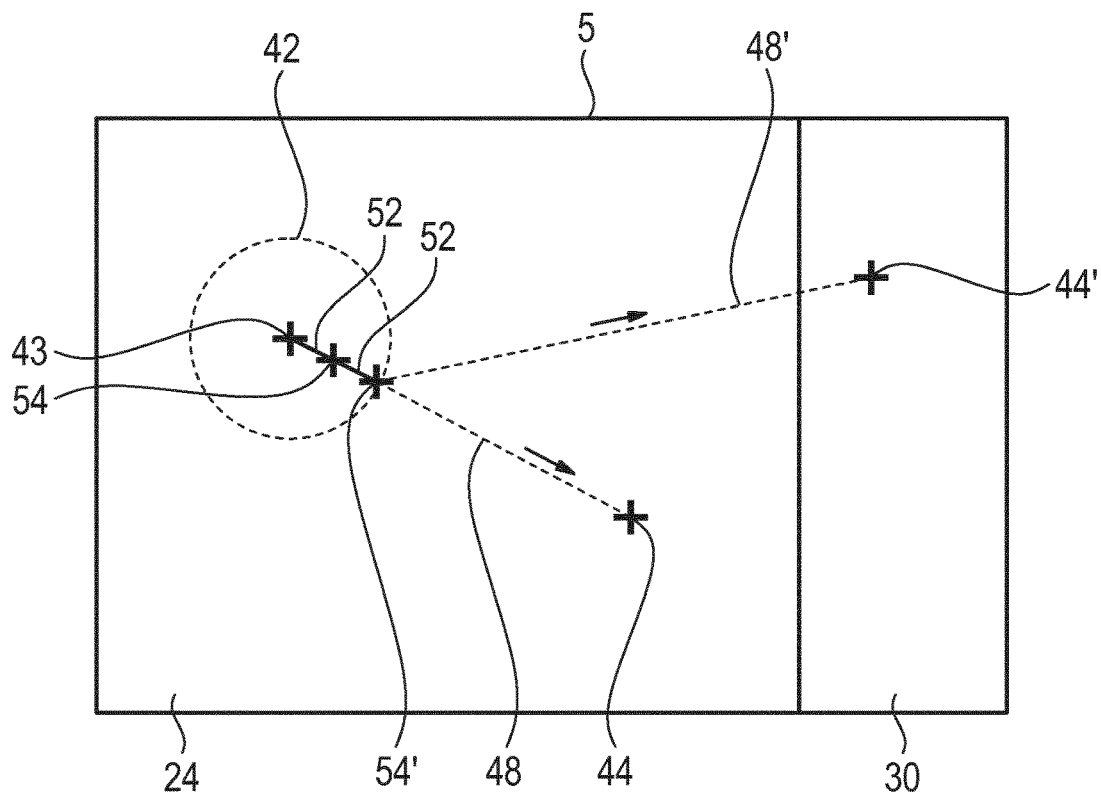
FIG. 3 shows a detail of a display on which an embodiment of the inventive method is being performed.

The process of moving the selected marker 42 is shown in more detail in FIG. 3. This figure shows an extract of image region 24, in which is placed the marker 42 having crosslines indicating the point 43. As the user touches or otherwise indicates the second point 44 on the display 5, the marker 42 will be moved from the first point 43 along the arrow 48 defined by a pointed line connecting the first point 43 and the second point 44, towards the third point 54. The direction 48 is determined by the relative position of first and second points 43, 44. The length by which the marker 42 is being moved is a defined distance 52. As described above, this defined distance 52 may be one unit length per touch or press of the user input event. According to an embodiment, the user may also use a "long press" or "long touch", i. e. he may prolong the mouse click or finger tap on the display 5, and the duration of this user input event will determine by how many unit lengths the marker 42 is being moved in direction 48. For example, the marker 42 may move in a stepwise manner, unit length by unit length, as long as the touch or press of the user input event lasts. In the example shown, the marker 42 is moved first along the defined distance 52 towards the third point 54. As the user input event is continued, the marker will be moved another defined distance 52 in the direction 48 towards third point 54'. If the touch or press is then released, this will be the final position of the marker 42. Of course, the inventive method may be iterated by a further input event at another second position 44', triggering a further movement of marker 42 in a different direction 48' towards the new second position 44'.

In a useful embodiment, the point of touch 44 need not be inside the image region 24, and in particular not inside the Region of Interest (e.g. a region showing a body part on which measurements are to be made). Rather, the point of touch 44 may also be outside the image region 24 and outside the Region of Interest at any position of the display, for example inside a measurement control area 30. By allowing the user to control movement of the marker 42 by touching the display 5 far away from the region of interest in which the marker 42 is placed, the user avoids to tap the region of interest with his/her hand, and thereby measurement accuracy is improved. In the example of FIG. 3, a second position 44' is outside the image region 24 in the measurement control area 30, far away from the marker 42.

To implement an embodiment of the invention, one needs to store the coordinates of the point 44 in the direction of which the user wants to move, and the coordinates of the center of the selected cursor 42. In a next step, the unit length 52 is obtained, e.g. from the input field 36 in the measurement control area, to determine the distance by which the marker 42 will move. In the next step, the algorithm explained below is run to calculate the coordinate of the third point 54 to move the selected marker 42 to. Then, the selected marker 42 is moved in the desired direction 48 by the defined distance 52, for example by a unit length.

Figure 4:
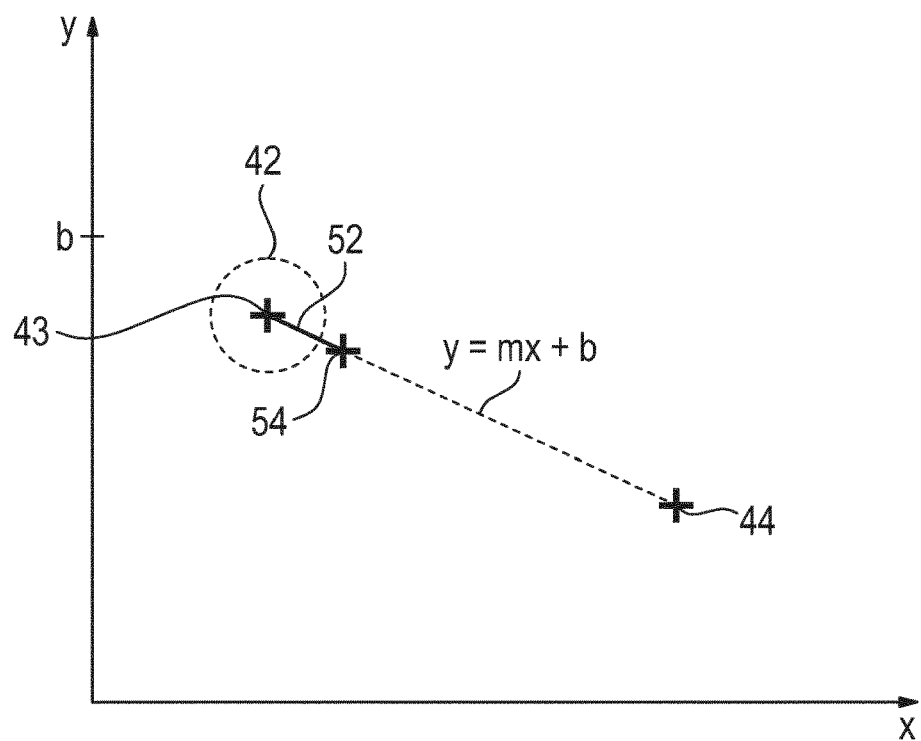
FIG. 4 shows a detail of a display illustrating the movement of the marker.

The algorithm is illustrated with regard to FIG. 4: If the coordinates of the first point 43 are (x1, y1) and the coordinates of the second point 44 are (x2, y2), the direction "m" in which the marker is moved according to an embodiment of the invention is $m=((y2-y1)/(x2-x1))$. The y intersect named "b" is $b=y1+(m*x1)$. Therefore, the equation of the line connecting the first and second point is $y=m*x+b$, which determines the points in the line to move the marker along the intended direction.

Figure 5:
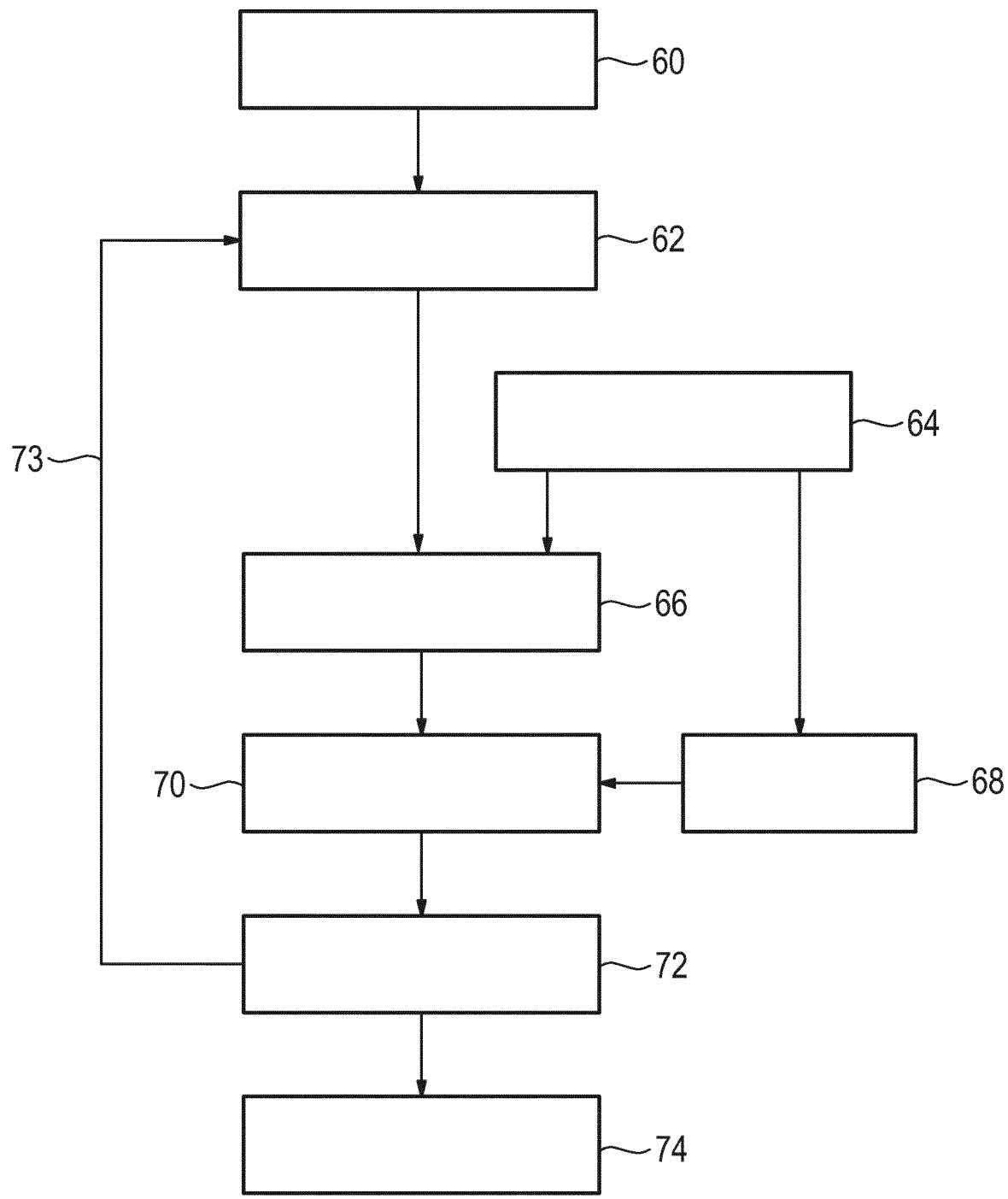
FIG. 5 shows a flow diagram illustrating the method steps according to an embodiment of the invention.

The method is further illustrated by the flow diagram of FIG. 5: In step 60, the marker 42 is selected, and it is at an initial position 43. Such initial position 43 may be reached by dragging the marker 42 on the display, e.g. by a conventional drag-and-drop method. Once the marker 42 is selected, the algorithm obtains the coordinates of the first point 43 indicated by the selected marker 43 in step 62. Step 64 indicates a user input event, by which a second position 44 on the display is selected, e.g. by means of a touch on the display 5, or the pressing of a cursor-movement device such as a mouse. In the next step 66, the coordinates of the second point 44 indicated by the user input event 46 are obtained by the algorithm. Further, in step 68, the length of the defined distance 52 is determined, for example by accessing an input field 36 containing a configurable unit length. Alternatively, or in addition, the defined distance 52 may be determined in step 68 by the duration of the user input event 64. For example, for a duration of the user input event of half a second, the marker 42 will be moved by one unit length (or one pixel). Accordingly, if the user input event 64 lasts for 10 seconds, the marker 42 will be moved by 20 pixels. In a preferred embodiment, this movement is not done in one large leap, but in a stepwise manner, so that the user has full control of the marker movement.

In the next step 70 the coordinates of the third point 54 to which the marker 42 is moved, is being determined. In the above example, this third point will be determined several times in step 70, and the marker 42 will be moved from one third point 54 to the next third point 54', each time by the unit distance of e.g. one pixel. As indicated by arrow 73, the method may return to step 62 to iterate the procedure as many times as desired by the user, so that the marker 42 will be moved again and again in any desired direction indicated by the second position. Once the marker 42 is placed exactly on the position desired by the user, e. g. a specific anatomical structure, the method may be concluded in step 74, e.g. by clicking on "end measurement" or by some other user input, and/or by unselecting the marker.

While the invention has been illustrated and described in detail in the drawings and foregoing description, such illustration and description are to be considered illustrative or exemplary and not descriptive; the invention is not limited to the disclosed embodiments.

REFERENCE SIGNS

1 Image evaluation device
2 monitor
4 medical image
5 display
6 processor
8 data storage medium
9 USB-stick
10 ultrasound control unit
12 ultrasound probe
14 patient bed
15 computer mouse
16 user
22 tablet computer
24 image region
26 anatomical structure
28 control bar
30 measurement control area
32 control buttons
34 slider
36 input field for unit length
38 home button
40 marker
41 point indicated by marker
42 selected marker
43 first point indicated by selected marker
44 second point
46 hand
48 direction defined by first and second points
52 defined distance
54 third point
60-74 process steps
60 select marker
62 obtain coordinates of first point
64 user input event
66 obtain coordinates of second point
68 determined length of defined distance 70 determined coordinates of third point
72 move marker to third point
74 unselect marker

The invention claimed is:

1. A method for precise positioning of a marker on a display, the method comprising the following steps:
  (a) Displaying an image and a marker overlaid on the image on a display, wherein the marker indicates a first point on the display, wherein the first point is located within an area indicated by displayed boundaries of the marker;
  (b) Obtaining the coordinates of a second point at a second position on the display, in response to a user input event indicating the second position;
  (c) Determining the coordinates of a third point on the display, said third point being located at a defined distance from the first point along a linear path between the first point to the second point, wherein the defined distance is one or several pixels of the display;
  (d) Moving the marker from the first point to the third point, so that the marker indicates the third point, thereby updating the position of the marker on the display, where in response to a second user input event at the second position, the marker moves from the third point towards the second point along the linear path between the first point and the second point by the defined distance.

2. The method of claim 1, wherein the length of the defined distance is configurable by the user input event.

3. The method of claim 1, wherein the user input event comprises at least one touch or press at the second position of the display.

4. The method of claim 1, wherein the defined distance has a pre-determined unit length or a multiple of said pre-determined unit lengths.

5. The method of claim 1, wherein the number of the defined distance increments moved by the first point towards the second point is configurable by the duration of the touch or press of the user input event.

6. The method of claim 1, wherein the marker moves from the first point towards the second point in a stepwise manner.

7. The method of claim 1, wherein the length of the defined distance is configurable by the distance of the second point from the first point.

8. The method of claim 1, wherein the marker is overlaid on an image displayed in an image region of the display, and the user input event comprises at least one touch or press at the second position on the display, the second position being inside or outside the image region.

9. The method of claim 1, wherein the coordinates of the third point are used to perform a measurement on the image displayed in the display.

10. The method of claim 1, wherein the image displayed on the display is a medical image.

11. A computer program comprising program code instructions which, when executed by a processor connected to a display, enables the processor to carry out the method according to claim 1.

12. A computer-readable medium comprising a computer program according to claim 11.

13. An image evaluation device configured to perform the method of claim 1, comprising:
  a display configured for displaying an image and a marker overlaid on the image, the marker indicating a first point on the display;
  a processor configured for obtaining the coordinates of the first point and of a second point at a second position on the display, in response to a user input event indicating the second position, and configured for determining the coordinates of a third point on the display, said third point being located at a defined distance from the first point in a direction defined by the first and second points;
  a pointing device configured for allowing a user to indicate the second position on the display.

14. The image evaluation device of claim 13, wherein the display is a touch-sensitive display, and the pointing device is constituted by the touch-sensitive display.

* * * * *